United States Patent
Gagnebien et al.

(10) Patent No.: US 6,461,621 B1
(45) Date of Patent: Oct. 8, 2002

(54) COSMETIC COMPOSITION IN THE FORM OF A MOLDED POWDER CAKE CONTAINING HOLLOW MICROCAPSULES AND THEIR PREPARATION

(75) Inventors: Didier Gagnebien, Chatillon; Béatrice DeFossez; Sophie Lecomte, both of Paris, all of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 08/258,575

(22) Filed: Jun. 10, 1994

Related U.S. Application Data

(63) Continuation of application No. 07/792,186, filed on Nov. 14, 1991, now abandoned.

(30) Foreign Application Priority Data

Nov. 15, 1990 (FR) ............................................. 90 14224

(51) Int. Cl.⁷ .......................... A61K 7/00; A61K 7/021; A61K 7/035
(52) U.S. Cl. ............................. 424/401; 424/63; 424/69
(58) Field of Search .............................. 424/63, 69, 401

(56) References Cited

U.S. PATENT DOCUMENTS

| | | | | |
|---|---|---|---|---|
| 2,797,201 A | * | 6/1957 | Veatch | 260/2.5 |
| 3,615,972 A | * | 10/1971 | Morehouse | 156/79 |
| 3,800,034 A | | 3/1974 | Kircher | 424/69 |
| 4,006,273 A | * | 2/1977 | Wolinski | 427/278 |
| 4,155,897 A | | 5/1979 | Schlusener | 523/500 |
| 4,944,937 A | * | 7/1990 | McCall | 424/65 |
| 4,952,402 A | | 8/1990 | Sparks | 424/423 |
| 5,000,947 A | | 3/1991 | Nichols | 424/69 |
| 5,024,831 A | | 6/1991 | Kuriaski | 424/69 |
| 5,030,446 A | | 7/1991 | Russ | 424/63 |
| 5,034,216 A | | 7/1991 | Barone | 424/69 |
| 5,035,885 A | * | 7/1991 | Arraudeau | 429/78 |
| 5,073,364 A | * | 12/1991 | Giezendanner | 424/63 |
| 5,219,561 A | * | 6/1993 | Gasnebien | 424/69 |
| 5,225,186 A | * | 7/1993 | Castrogiovanni | 424/64 |

FOREIGN PATENT DOCUMENTS

| | | |
|---|---|---|
| EP | 0211298 | 2/1987 |
| EP | 0254612 | 1/1988 |

OTHER PUBLICATIONS

Webster's Ninth New Collegiate Dictionary, 1990, p. 429.*

* cited by examiner

Primary Examiner—Thurman K. Page
Assistant Examiner—S. Tran
(74) Attorney, Agent, or Firm—Nixon & Vanderhye P.C.

(57) ABSTRACT

Solid cosmetic composition in the form of a molded powder cake includes a particulate charge containing hollow microspheres having one or more open or closed cavities. The weight proportion of the hollow microspheres ranges from 0.1 to 50 percent relative to the total weight of the composition. A process for the preparation of the composition and the use of such a particulate charge, dispersed in a non-aqueous liquid vehicle, for the preparation of a fluid paste intended for the preparation of such a solid cosmetic composition is also disclosed.

15 Claims, No Drawings

COSMETIC COMPOSITION IN THE FORM OF A MOLDED POWDER CAKE CONTAINING HOLLOW MICROCAPSULES AND THEIR PREPARATION

This is a continuation of application Ser. No. 07/792,186, filed Nov. 14, 1991, now abandoned.

The present invention relates to a solid cosmetic composition in the form of a molded powder cake comprising as a principal particulate charge hollow microspheres having one or more open or closed cavities.

The invention also concerns a process for producing such a molded powder cake.

It is known that certain makeup products in the form of solid powder cosmetic products, such as eyelid makeup or cheek makeup are generally provided in the form of molded powder cakes. A "molded powder cake" is one which is produced by mixing a solid particulate phase and a binding agent (generally a fatty phase) in a solvent, so as to obtain a fluid paste, distributing the said fluid paste by pouring it into appropriate containers (dishes or cups) and then evaporating the solvent. The advantages of molded powder cakes are on the one hand the possibility of introducing various ingredients into the composition owing to the choice of the solvent selected, and on the other hand, the free choice of the form and material of the cup or dish, which permits multiple presentations of the final products.

In the preparation of molded powder cakes, several kinds of disadvantages are observed: a shrinkage phenomenon which results in the cup or dish not being completely filled (which is discouraging to the consumer); an irregular appearance of the surface of the product (a grooved, cracked or cratered appearance at the time of evaporation); and formation of a film of the binding agent on the surface.

Various solutions have been proposed to remedy these disadvantages.

In EP patent application No. 0038645, the cup, the open upper portion of which is fitted with a removable lid, is filled, in inverse position, by the base which is constituted by a support in the form of a grid. After evaporation of the solvent, the base is sealed with an appropriate base plate. In this manner, the irregular appearance of the surface through which is produced the evaporation of the solvent, as well as the shrinkage phenomenon, are not visible to the consumer. This procedure exhibits the disadvantage of requiring a special cup with the base support in the form of a grid.

U.S. Pat. No. 4,804,538 envisages the use of a cup the base of which has openings for filling with the fluid paste through the base, in non-inverse position, using injection nozzles fed under pressure, while the solvent is evaporated through the upper portion of the cup linked to a vacuum pump. This procedure requires complex and costly equipment.

In EP patent application No. 0165137 there is proposed the use of, as a binder, a bentonite treated with a cationic surfactant. Since this binder is not soluble in the solvent, the formulation of a surface film of the binding agent is avoided. However, the problem of shrinkage is not resolved and the feel of the resulting product is not satisfactory.

DE 332701 patent describes a process for preparing molded powder cakes in which the various operations of mixing the ingredients with an excess of solvent, molding and evaporation of solvent are effected hot increase the production costs. According to this patent, the condition of the surface of the molded powder cake is improved. However, the shrinkage phenomenon is not avoided.

It has now been discovered that the addition, as a constituent of the particulate charge, of a small weight amount of hollow microspheres having one or more open or closed cavities, permits the preparation, with a significant reduction of the shrinkage phenomenon, of molded powder cakes having a satisfactory surface condition and disintegration.

It has also been evidenced that the use of these novel constituents of the particulate charge permits the preparation at a moderate temperature and with a choice of various solvents, which indeed provides advantages on the economic level.

The invention thus relates to a solid cosmetic composition in the form of a molded powder cake constituted by a solid particulate phase and optionally a binder agent and conventional additives, wherein the particulate phase includes hollow microspheres having one or more open or closed cavities.

It has been noted that by practicing the invention a solid powder having a satisfactory surface condition and disintegration and a very small amount of shrinkage can be obtained. It will be noted here, as is well known to the specialists, that molded powder cakes have the appearance and the properties of a coherent solid product, having principally a defined surface as opposed to free powders (free flowing). Since it is a question of coherent solid products, their use requires the removal of a certain amount of powder by disintegration using an appropriate applicator.

The microspheres employed here are particles of essentially spherical form having generally a diameter less than 70 $\mu$m (preferably less than 40 $\mu$m).

The microspheres are produced from any appropriate inorganic or organic material, compatible with a use on the skin, that is, nonirritating and nontoxic.

The microspheres of an organic polymer material possessing a single closed cavity containing a gas, such as a hydrocarbon (for example, isobutane), can be prepared in accordance with known procedures, for example, those described in U.S. Pat. No. 3,615,972 and in EP patent application 0056219.

The organic microspheres are produced, for example, from polymers or copolymers derived from acids, amides or esters (monomers) having ethylenic unsaturation, from urea-formaldehyde polymers, from polymers or copolymers of vinylidene chloride, etc.

Mention can be made, as an example, of microspheres made from acrylate or methyl methacrylate polymers or copolymers, or even from vinylidene chloride/acrylonitrile copolymers.

Representative vinylidene chloride/acrylonitrile copolymers include principally those which contain, by weight, from 20 to 60 percent of units derived from vinylidene chloride, from 20 to 60 weight percent of units derived from acrylonitrile and from 0 to 40 weight percent of other units such as units derived from an acrylic or styrene monomer.

There can even be used crosslinked acrylic polymers or copolymers, for example, polymers the carboxylic groups of which are partially esterified with diols serving as crosslinking agents.

These materials can serve as a base for the preparation of microporous microspheres.

When the hollow microspheres employed in accordance with the invention are microporous microspheres, their range corresponds, for example, to a specific surface of at least 0.5 m$^2$/g, and in particular of at least 1 m$^2$/g. There is no upper limit (other than that resulting from the possibility of practical production of the microspheres having a very high porosity) for the specific surface. The specific surface can extend, for example, to 1000 m$^2$/g or even higher, for example, up to a few hundreds of thousands of m$^2$/g.

Particularly preferred are principally the microporous microspheres sold by Dow Corning under the trade name "POLYTRAP Q5-6603", or those sold by Seppic under the trade name "MICROPEARL M" or "MICROPEARL M100", as well as hollow microspheres having a closed cavity sold under the trade name "EXPANCEL" by Kemanord Plast.

Representative microspheres derived from an inorganic material, include, for instance, silica microspheres having open porosity or, preferably, hollow, such as for example those sold under the trade name "SILICA BEADS S700" by Miyoshi Kasei Inc.

Preferably, microspheres having a density (more exactly a volume mass) lower than 0.7 g/cm$^3$, for example between 0.01 and 0.7 g/cm$^3$ are employed. The volume mass of the powders depend on their degree of packing. The volume masses given here correspond to the volume mass measured in accordance with the German standard DIN 53194, after ten packings.

The weight amount of the hollow microspheres in the molded powder cake ranges generally from 0.2 to 15 percent relative to the total weight of the composition with the solvent (fluid paste).

Concerning the amount of the hollow microspheres in the dried final composition, it can vary generally from 0.1 to 50 percent, preferably from 0.5 to 15 percent relative to the total weight of the composition after evaporation of the solvent.

The composition in the form of a molded powder cake containing the above defined microspheres can also contain pigments and/or other complementary charges. It is a question indeed of nonhollow particulate particles (in other words, those which essentially do not have any open or closed cavities), the dimension of which does not exceed about 200 $\mu$m.

The complementary pigments and/or charges are those conventionally employed in cosmetic compositions in the form of solid powders. The pigments are selected principally from mineral pigments, organic pigments or their mixtures.

Representative mineral pigments include, for example:
  titanium dioxide (rutile or anatase) optionally surface treated and listed in Color Index under the reference CI 77891;
  black, yellow, red and brown iron oxides, listed under references CI 77499, 77492 and 77491;
  manganese violet (CI 77742);
  ultramarine blue (CI 77007);
  hydrated chromium oxide (CI 77289) and
  ferric blue (CI 77510).

Representative organic pigments, include, in particular, the following pigments:
  D&C Red No. 19 (CI 45170);
  D&C Red No. 9 (CI 15585);
  D&C Red No. 21 (CI 45380);
  D&C Orange No. 4 (CI 15510);
  D&C Orange No. 5 (CI 45370);
  D&C Red No. 27 (CI 45410);
  D&C Red No. 13 (CI 15630);
  D&C Red No. 7 (CI 15850-1);
  D&C Red No. 6 (CI 15850-2);
  D&C Yellow No. 5 (CI 19140);
  D&C Red No. 36 (CI 12085);
  D&C Orange No. 10 (CI 45425);
  D&C Yellow No. 6 (CI 15985);
  D&C Red No. 30 (CI 73360);
  D&C Red No. 3 (CI 45430);
  Carbon black (CI 77266); and
  carmine or cochineal based lakes (CI 75470).

Nacreous pigments can also be employed and can be selected principally from
  white nacreous pigments, such as mica coated with titanium oxide, bismuth oxychloride; and
  colored nacreous pigments, such as mica titanium with iron oxides, mica titanium with ferric blue, or chrome oxide, mica titanium with an organic pigment of the above mentioned type, as well as those based on bismuth oxychloride.

The pigment can represent up to 50 weight percent of the total weight of the fluid paste.

The complementary charges are selected principally from:
  talc, which is hydrated magnesium silicate, employed in particulate form, generally having a size lower than 40 $\mu$m; the talc possesses humidity absorbing properties and is employed especially because of its unctuous feel or touch;
  micas, which are alumino silicates of various compositions, which are provided in the form of flakes having a size ranging from 2 to 200 $\mu$m, preferably from 5 to 70 $\mu$m and a thickness of 0.1 to 5 $\mu$m, preferably 0.2 to 3 $\mu$m. The micas can be of natural origin (for example, muscovite, margarite, roscoelithe, lepidolithe, biotite) or of synthetic origin. The micas are generally transparent and permit to confer to the skin a satiny appearance;
  starch, in particular rice starch;
  kaolin, which is a hydrated aluminum silicate, which is provided in the form of particles of isotrope form having a size generally lower than 30 Am, and which possesses good fatty body absorption properties;
  oxides of zinc and titanium, generally employed in particulate form having a size not exceeding a few micrometers (or even lower than 1 $\mu$m in the case of titanium oxide); these oxides have an unctuous feel or touch, have good covering power and have a significant opacity;
  precipitated calcium carbonate which, in the form of particles having a size lower than 10 $\mu$m, have an unctuous touch and permit to obtain a matte appearance;
  magnesium carbonate or bicarbonate which possesses, principally, perfume fixation properties;
  metallic soaps derived from an organic carboxylic acid having from 8 to 22 carbon atoms, preferably from 12 to 18 carbon atoms, for example, zinc stearate, magnesium stearate, lithium stearate, zinc laurate, magnesium myristate and the like. These soaps, generally provided in the form of particles having a size lower than 10 $\mu$m have an unctuous feel or touch and facilitate the adherence of the powder to the skin;
  synthetic polymeric powders, such as polyethylene, polyesters (for example, polyethylene isophthalate or polyethylene terephthalate), polyamides under the form of particles having a size lower than 50 $\mu$m, which possess absorbent properties, and permit to impart to the skin a velvety appearance.

These complementary charges can represent up to 65 weight percent of the total weight of the fluid paste.

The nonaqueous liquid vehicle (generally called "solvent") employed to suspend the various constituents can be selected, for example, from the group constituted by:

alcohols (such as ethanol or isopropanol); straight or branched chain alkanes such as hexane, pentane, heptane or isoparaffin; the cyclic alkanes (such as cyclohexane); volatile silicones (for example, the cyclodimethicones); chlorinated solvents (such as dichloromethane or dichloroethane); and their mixtures. This solvent represents 30 to 70 weight percent of the fluid paste, and preferably 45 to 65 weight percent.

Preferably, as mentioned above, the suspension contains a fatty or oily phase which can act as a binder. This fatty phase is constituted by at least one fatty body, liquid or solid at ambient temperature and/or at least one oil soluble synthetic polymer the use of which in cosmetics is known.

Representative fatty bodies, liquid at ambient temperature, include mineral, animal, vegetable or synthetic oils, or even silicone oils. It is a question, for example, of petrolatum oil, liquid lanolin, arara oil, sesame oil, macadamia oil or jojoba oil and synthetic triglycerides.

Representative oil soluble synthetic polymers, include polyvinylpyrrolidone/hexadecene or PVP/eicosene copolymers such as the products sold by GAF Corp. under the trade names "GANEX V-216" and "GANEX V-220".

The fatty phase generally represents from 0 to 20 percent by weight relative to the total weight of the fluid paste.

Various other additives can be introduced into the fluid paste, such as: sunscreen agents; softening agents; hydrating agents (sorbitol, glycerine); cicatrisive agents; anti-free radical agents; vitamins, perfumes and the like.

Finally, water-soluble consistency agents such as natural or synthetic gums, cellulose derivatives or acrylic polymers can be added during the course of preparing the fluid paste.

The cosmetic composition of the invention is prepared by a process comprising dispersing in a nonaqueous liquid vehicle a particulate phase and optionally a binding agent and conventional additives so as to obtain a homogeneous fluid paste, distributing the said fluid paste into appropriate containers, and evaporating the said liquid vehicle, wherein the said particulate phase includes hollow microspheres having one or more open or closed cavities.

The process of the invention comprises then, in a first stage, introducing the various constituents in a liquid vehicle. To suspend the various constituents of the cosmetic product in this solvent, it is possible to previously mix the powder constituents among themselves and the constituents of the fatty phase between themselves. However it is also possible to introduce the various constituents into the solvent in any order. The mixture is then homogenized generally at ambient temperature. This mixture is then directly molded in cups, preferably at ambient temperature. Finally the solvent is evaporated. To do so the cups are placed in an oven, preferably at a temperature not exceeding about 40° C., for a time sufficient which can vary from 6 to 60 hours.

The following nonlimiting examples are given to illustrate the invention.

EXAMPLE 1

Eyelid Makeup

| Phase A | |
|---|---|
| Talc | 9.7 |
| Chromium oxide | 1.8 |
| Ultramarine blue | 0.7 |
| Zinc stearate | 0.7 |
| Mica | 5.3 |
| Starch | 1.7 |
| Micatitanium | 10.5 |
| "EXPANCEL 551 DE", sold by Kemanord Plast | 1.4 |
| Phase B | |
| Polyvinylpyrrolidone/hexadecene copolymer | 0.2 |
| Jojoba oil | 0.5 |
| Isopropyl myristate | 0.7 |
| Lanolin | 0.4 |
| Sweet almond oil | 1.2 |
| Preservatives | |
| Butylhydroxytoluene (BHT) | 0.015 |
| Butylhydroxyanisole (BHA) | 0.015 |
| Propyl parahydroxybenzoate | 0.1 |
| Solvent | |
| Cyclomethicone | 65 |

The "EXPANCEL 551 DE" powder is constituted by hollow microspheres (single cavity) of a vinylidene chloride/acrylonitrile copolymer (specific volume 0.02 g/cm$^3$).

To produce this eyelid makeup, the following procedures are carried out:

In a first stage the constituents of phase B are mixed together. Moreover the constituents of phase A are introduced into a mixer followed by introduction of the solvent. The whole is then homogenized.

Then phase B, to which have been added the preservatives (BHT, BHA and propyl parahydroxybenzoate) is introduced in its turn into the mixer and the whole is mixed until a homogeneous paste is obtained. The paste is then molded in metallic cups at ambient temperature. These cups are then placed in an oven at 40° C. for 55 hours. At the end of this period, a blue-green eyelid makeup is obtained, the surface of which is smooth and homogenous and which is particularly easy to apply.

EXAMPLE 2

Eyelid Makeup

| Phase A | |
|---|---|
| Talc | 13.4 |
| Iron oxides | 5.8 |
| Micatitanium | 13.7 |
| "EXPANCEL 551 DE", sold by Kemanord Plast | 2.0 |
| Phase B | |
| Petrolatum oil | 2.0 |
| Lanolin | 2.0 |
| Preservative | |
| Propyl parahydroxybenzoate | 0.1 |
| Solvent | |
| Cyclohexane | 61 |

To produce this eyelid makeup the following procedures are carried out:

Phase A and phase B are mixed with the solvent, in the mixer, which is stirred until a homogenous paste is obtained. The powder is molded in metallic cups at ambient temperature. The cups are then placed in a stove at 40° C. for 20 hours.

In an analogous manner, an eyelid makeup according to the invention is prepared by replacing the petrolatum oil and lanolin by 4 g of stearyldimethicone.

EXAMPLE 3

Cheek Makeup

| | |
|---|---|
| Phase A | |
| Talc | 20.8 |
| Titanium dioxide | 3.5 |
| Colored micatitanium | 16 |
| DC Red 30 | 0.1 |
| "POLYTRAP Q5-6603" by Dow Corning | 1.5 |
| Phase B | |
| Petrolatum oil | 2.5 |
| Jojoba oil | 0.5 |
| Preservative | |
| Propyl parahydroxybenzoate | 0.1 |
| Solvent | |
| Ethanol | 55 |

The "POLYTRAP Q5-6603" powder is constituted of hollow microspheres of a crosslinked acrylate copolymer, having open cavities (about 13.6 percent of the total volume; a specific surface of about 9.6 m$^2$/g).

To produce this cheek makeup, the procedures set forth in Example 1 are followed.

In an analogous manner, a cheek makeup according to the invention is prepared by replacing the jojoba oil with the same amount of caprylic/capric triglyceride.

EXAMPLE 4

Face Powder

| | |
|---|---|
| Phase A | |
| Talc | 27.3 |
| Iron oxides | 4 |
| Starch | 2 |
| Titanium dioxide | 1.5 |
| "MICROPEARL M100", sold by Seppic | 3.5 |
| Mica | 9 |
| Phase B | |
| Isopropyl myristate | 1.5 |
| Petrolatum oil | 0.6 |
| Sorbitol | 0.4 |
| Preservatives | |
| Propyl parahydroxybenzoate | 0.1 |
| Butylhydroxyanisole | 0.05 |
| Butylhydroxytoluene | 0.05 |
| Solvent | |
| Isoparafin hydrocarbons | 50 |

The "MICROPEARL M100" powder is constituted of methyl polymethacrylate microspheres having open cavities (specific surface: about 0.9–1 m$^2$/g).

To prepare this face powder, procedures analogous to those described in EXAMPLE 1 are followed.

EXAMPLE 5

Face Powder

| | |
|---|---|
| Phase A | |
| Talc | 29 |
| Bismuth oxychloride | 6 |
| Titanium dioxide | 4 |
| Starch | 6.5 |
| Iron oxides | 2 |
| "POLYTRAP Q5-6603" | 3.5 |
| Phase B | |
| Jojoba oil | 1.5 |
| Lanolin | 0.5 |
| Solvent | |
| Isopropanol | 47 |

To prepare this face powder procedures analogous to those described in EXAMPLE 1 are followed.

EXAMPLE 6

Perfumed Body Powder

| | |
|---|---|
| Phase A | |
| Talc | 33.37 |
| Iron oxides | 0.05 |
| Zinc stearate | 1.5 |
| "POLYTRAP Q5-6603" | 1 |
| Phase B and Preservatives | |
| Propyl parahydroxybenzoate | 0.08 |
| Perfume | 2 |
| Solvent | |
| Dichloromethane | 62 |

To prepare this perfumed body powder, procedures analogous to those of EXAMPLE 1 are carried out.

EXAMPLE 7

Eyelid Makeup

| | |
|---|---|
| Phase A | |
| Chromium oxide | 5.88 |
| Micatitanium | 13.72 |
| Talc | 14.94 |
| "EXPANCEL 551 DE" | 1.18 |
| Phase B and Preservative | |
| Petrolatum oil | 2.12 |
| Lanolin | 0.19 |
| Oleic alcohol | 0.39 |
| Petrolatum | 0.39 |
| Isopropyl myristate | 0.31 |
| Propyl parahydroxybenzoate | 0.08 |
| Solvent | |
| Cyclohexane | 60.8 |

To prepare this eyelid makeup, procedures analogous to those of EXAMPLE 1 are followed.

EXAMPLE 8

Eyelid Makeup

| Phase A | |
|---|---|
| Chromium oxide | 5.88 |
| Micatitanium | 13.72 |
| Talc | 14.94 |
| "POLYTRAP Q5-6603" | 1.18 |
| Phase B and Preservative | |
| Petrolatum oil | 2.12 |
| Lanolin | 0.19 |
| Oleic alcohol | 0.39 |
| Petrolatum | 0.39 |
| Isopropyl myristate | 0.31 |
| Propyl parahydroxybenzoate | 0.08 |
| Solvent | |
| Cyclohexane | 60.8 |

To prepare this eyelid makeup, procedures analogous to those described in EXAMPLE 1 are followed.

EXAMPLE 9

Eyelid Makeup

| Phase A | |
|---|---|
| Chromium oxide | 5.88 |
| Micatitanium | 13.72 |
| Talc | 14.94 |
| "MICROPEARL M-100" | 1.18 |
| Phase B and Preservative | |
| Petrolatum oil | 2.12 |
| Lanolin | 0.19 |
| Oleic alcohol | 0.39 |
| Petrolatum | 0.39 |
| Isopropyl myristate | 0.31 |
| Propyl parahydroxybenzoate | 0.08 |
| Solvent | |
| Cyclohexane | 60.8 |

To prepare this eyelid makeup, procedures analogous to those described in Example 1 are followed.

EXAMPLE 10

Eyelid Makeup

| Phase A | |
|---|---|
| Chromium oxide | 5.88 |
| Micatitanium | 13.72 |
| Talc | 14.94 |
| "SILICA BEADS SB700" | 1.18 |
| Phase B and Preservatives | |
| Petrolatum oil | 2.12 |
| Lanolin | 0.19 |
| Oleic alcohol | 0.39 |
| Petrolatum | 0.39 |
| Isopropyl myristate | 0.31 |
| Propyl parahydroxybenzoate | 0.08 |
| Solvent | |
| Cyclohexane | 60.8 |

The "SILICA BEADS SB700" powder is a particulate powder of porous silica having a central cavity (specific surface; about 600–800 m$^2$/g).

To prepare this eyelid makeup, procedures analogous to those described in EXAMPLE 1 are carried out.

Comparison Examples

The following Examples 11 to 14 are comparison examples.

EXAMPLE 11

Eyelid Makeup

| Phase A | |
|---|---|
| Chromium oxide | 5.88 |
| Micatitanium | 13.72 |
| Talc | 14.94 |
| Polyamide powder, sold under the trade name "RILSAN D 50 NAT" by Atochem | 1.18 |
| Phase B and Preservative | |
| Petrolatum oil | 2.12 |
| Lanolin | 0.19 |
| Oleic alcohol | 0.39 |
| Petrolatum | 0.39 |
| Isopropyl myristate | 0.31 |
| Propyl parahydroxybenzoate | 0.08 |
| Solvent | |
| Cyclohexane | 60.8 |

To prepare this eyelid makeup, procedures analogous to those described in EXAMPLE 1 are followed.

EXAMPLE 12

Eyelid Makeup

| Phase A | |
|---|---|
| Chromium oxide | 5.88 |
| Micatitanium | 13.72 |
| Talc | 14.94 |
| Polyethylene powder, sold under the trade name "COATHYLENE HA 1681" by Plast-Labor | 1.18 |
| Phase B and Preservative | |
| Petrolatum oil | 2.12 |
| Lanolin | 0.19 |
| Oleic alcohol | 0.39 |
| Petrolatum | 0.39 |
| Isopropyl myristate | 0.31 |
| Propyl parahydroxybenzoate | 0.08 |
| Solvent | |
| Cyclohexane | 60.8 |

To prepare this eyelid makeup, procedures analogous to those described in EXAMPLE 1 are followed.

EXAMPLE 13

Eyelid Makeup

| Phase A | |
|---|---|
| Chromium oxide | 5.88 |
| Micatitanium | 13.72 |
| Talc | 14.94 |
| Polyvinylpyrrolidone, powder sold under the trade name "PVP K-30" by GAF Corp. | 1.18 |
| Phase B and Preservative | |
| Petrolatum oil | 2.12 |
| Lanolin | 0.19 |
| Oleic alcohol | 0.39 |
| Petrolatum | 0.39 |
| Isopropyl myristate | 0.31 |
| Propyl parahydroxybenzoate | 0.08 |
| Solvent | |
| Cyclohexane | 60.8 |

To prepare this eyelid makeup, procedures analogous to those described in EXAMPLE 1 are followed.

EXAMPLE 14

Eyelid Makeup

| Phase A | |
|---|---|
| Chromium oxide | 5.88 |
| Micatitanium | 13.72 |
| Talc | 14.94 |
| Pulverulent tricalcium phosphate | 1.18 |
| Phase B and Preservative | |
| Petrolatum oil | 2.12 |
| Lanolin | 0.19 |
| Oleic alcohol | 0.39 |
| Petrolatum | 0.39 |
| Isopropyl myristate | 0.31 |
| Propyl parahydroxybenzoate | 0.08 |
| Solvent | |
| Cyclohexane | 60.8 |

To prepare this eyelid makeup, procedures analogous to those described in EXAMPLE 1 are followed.

Comparative Tests

In order to evidence the qualities of the cosmetic products obtained in accordance with the present invention, comparative tests have been carried out.

These tests consist in comparing four compositions according to the present invention (Examples 7–10) with four compositions in which the microspheres were replaced by conventional charges or fillers (constituted of particles not having closed or open cavities), to wit, a nylon powder, a polyethylene powder, polyvinylpyrrolidone and tricalcium phosphate (examples 11–14, respectively).

The tests were carried out to study (1) disintegration and (2) shrinkage in the container.

(1) Disintegration

Disintegration is studied using a disintegration apparatus consisting of an arm driven by a rotary disk and equipped with an applicator at one of its ends. This applicator is placed on the surface of the molded and dried product where it effects a determined number of rotations. The apparatus permits to exercise a constant force on the molded product. The average weight loss on three containers after 10 disintegration turns is measured. The disintegration, characterized by the weight loss ($\Delta p$) in grams for each of the eight compositions tested is given in the Table below.

(2) Shrinkage in the Container

In order to determine the filling height of the container after evaporation of the solvent, the INTERAPID comparator (Ludwig Metrologie 1515, Roch company) is employed which permits to measure a thickness ranging up to 10 mm with a precision of $10^{-2}$ mm.

For each of the eight compositions, there has been effected a series of five measurements per container, repeated on six containers that is an average total over thirty measurements.

Thus the average filling height of the container is established. This height, divided by the height of the container employed (4 mm) gives the amount of filling (R, expressed in percent) of the container after drying. The amount of shrinkage is the difference between 100% and R. The amount of filling for each composition are given in the Table below.

| Example | p (g) | R (%) |
|---|---|---|
| Invention | | |
| 7 | $4 \times 10^{-3}$ | 99.7 |
| 8 | $6 \times 10^{-3}$ | 89.7 |
| 9 | $10 \times 10^{-3}$ | 88.3 |
| 10 | $10 \times 10^{-3}$ | 89.0 |
| Comparison | | |
| 11 | $22 \times 10^{-3}$ | 50.5 |
| 12 | $20 \times 10^{-3}$ | 57.2 |
| 13 | $21 \times 10^{-3}$ | 51.5 |
| 14 | $23 \times 10^{-3}$ | 50.5 |

The results show that the loss in weight of the composition according to the invention is reduced relative to that of the comparison compositions which are too powdery.

It is also remarkable that the compositions according to the invention result in a better filling value than the comparison composition. The amount of shrinkage involved with the compositions of the present invention does not exceed about 10%, whereas it is close to 50% for the comparison compositions.

What is claimed is:

1. A cosmetic molded powder cake composition consisting essentially of: hollow microspheres having at least one cavity and being present in an amount ranging from 0.1 to 50 percent by weight relative to the total weight of said molded powder cake composition, at least one non-hollow particle pigment acceptable for cosmetic compositions, at least one fatty or oily binder, and at least one non-hollow particle complementary charge acceptable for cosmetic compositions; said hollow microspheres having a diameter of less than 70 $\mu$m, and said binder being present in an amount of up to 20% by weight of said composition.

2. The molded powder cake composition of claim 1, wherein said hollow microspheres have a volume mass lower than 0.7 g/cm$^3$.

3. The molded powder cake composition of claim 1 wherein said hollow microspheres have a diameter less than 40 $\mu$m.

4. The molded powder cake composition of claim 1 wherein said microspheres are porous microspheres having a specific surface area of at least 0.5 $m^2/g$.

5. The molded powder cake composition of claim 1 wherein said microspheres are porous microspheres having a specific surface area of at least 1 $m^2/g$.

6. The molded powder cake composition of claim 1 wherein said microspheres are present in an amount ranging from 0.5 to 15 percent by weight relative to the total weight of said composition.

7. The molded powder cake composition of claim 1 wherein said hollow microspheres are made of vinylidene chloride/acrylonitrile copolymer.

8. The molded powder cake composition of claim 1 wherein said hollow microspheres are made of a cross-linked acrylic polymer or copolymer.

9. The molded powder cake composition of claim 1 wherein said hollow microspheres are made of methyl polymethacrylate polymer or copolymer.

10. A process for preparing a cosmetic molded powder cake composition consisting essentially of: hollow microspheres having at least one cavity and being present in an amount ranging from 0.1 to 50 percent, at least one non-hollow particle pigment acceptable for cosmetic compositions, at least one fatty or oily binder, and at least one non-hollow particle complementary charge acceptable for cosmetic compositions; said process comprising the steps of: dispersing said hollow microspheres, non-hollow particle pigment, fatty or oily binder, and non-hollow particle complementary change in an evaporative non-aqueous liquid so as to obtain a homogeneous fluid paste; introducing said homogeneous fluid paste into a container having a form corresponding to the form of the resulting cohesive solid cake and evaporating said evaporative non-aqueous liquid so as to obtain said composition, wherein said hollow microspheres have a volume mass less than 0.7 $g/cm^3$ and are added in order to reduce shrinkage and maintain a satisfactory surface condition of said composition.

11. The process of claim 10 wherein said evaporative non-aqueous liquid is evaporated at a temperature not exceeding 40° C.

12. The process of claim 10, wherein said evaporative non-aqueous liquid is selected from the group consisting of an alcohol, a straight or branched chain alkane, a cyclic alkane, a volatile silicone, a chlorinated solvent and mixtures thereof.

13. The process of claim 12, wherein said evaporative non-aqueous liquid is selected from the group consisting of ethanol, isopropanol, cyclohexane, hexane, pentane, heptane, an isoparaffin, a cyclomethicone, dichloromethane and dichloroethane.

14. A cosmetic molded powder cake composition consisting essentially of: hollow microspheres having at least one cavity and being present in an amount ranging from 0.1 to 50% by weight relative to the total weight of said composition, at least one non-hollow particle pigment acceptable for cosmetic compositions, at least one oily binder, and at least one non-hollow particle complementary charge acceptable for cosmetic compositions; said hollow microspheres having a diameter of less than 70 $\mu$m, and said binder being present in an amount of up to 20% by weight of said composition.

15. In a method of preparing a cosmetic powder cake in the form of a molded powder cake wherein the improvement comprises adding as a filler a particulate charge containing hollow microspheres having one or more open or closed cavities, said filler being present in an amount of from about 0.1 to 50% by weight of the cosmetic powder cake whereby the amount of shrinkage is reduced and a satisfactory surface condition and disintegration condition are obtained.

* * * * *